United States Patent [19]
Duncan et al.

[11] Patent Number: 5,985,916
[45] Date of Patent: Nov. 16, 1999

[54] POLYMER-PLATINUM COMPOUNDS

[75] Inventors: Ruth Duncan, London, United Kingdom; Paolo Ferruti, Milan, Italy; Evagoras G. Evagorou, London, United Kingdom

[73] Assignee: Access Pharmaceuticals, Inc., Dallas, Tex.

[21] Appl. No.: 09/062,372

[22] Filed: Apr. 17, 1998

Related U.S. Application Data

[60] Provisional application No. 60/044,701, Apr. 18, 1997.

[51] Int. Cl.$^6$ .................................................. A61K 31/28
[52] U.S. Cl. ............................... 514/492; 514/8; 514/54; 514/184; 556/136; 556/137; 536/101
[58] Field of Search ..................... 556/136, 137; 514/8, 54, 184, 492; 536/101

[56] References Cited

U.S. PATENT DOCUMENTS

| | | | |
|---|---|---|---|
| 4,062,831 | 12/1977 | Kopecek et al. | 526/208 |
| 4,097,470 | 6/1978 | Drobnik et al. | 525/54.11 |
| 5,037,883 | 8/1991 | Kopecek et al. | 525/54.1 |
| 5,362,831 | 11/1994 | Mongelli et al. | 526/304 |
| 5,420,105 | 5/1995 | Gustavson et al. | 514/2 |
| 5,473,055 | 12/1995 | Mongelli et al. | 530/329 |
| 5,547,667 | 8/1996 | Angelucci et al. | 424/181.1 |
| 5,569,720 | 10/1996 | Mongelli et al. | 525/329.4 |
| 5,629,384 | 5/1997 | Veronese et al. | 525/326.8 |
| 5,631,322 | 5/1997 | Veronese et al. | 525/54.1 |
| 5,631,336 | 5/1997 | Ferruti et al. | 526/264 |

FOREIGN PATENT DOCUMENTS

| | | |
|---|---|---|
| 187547 B1 | 7/1986 | European Pat. Off. . |
| 190464 A2 | 8/1986 | European Pat. Off. . |
| 2034856 | 5/1995 | Russian Federation . |
| WO 88/00837 | 2/1988 | WIPO . |
| WO 92/10212 | 6/1992 | WIPO . |
| WO93/13804 | 7/1993 | WIPO . |
| WO 94/02106 | 2/1994 | WIPO . |
| WO 94/07536 | 4/1994 | WIPO . |
| 96/00079 | 1/1996 | WIPO . |

OTHER PUBLICATIONS

Bogdanov, A.A., et al., "An Adduct of cis–Diamminedichloroplatinum(II) and poly(ethylene glycol)poly(L–lysine-)–Succinate: Synthesis and Cytotoxic Properties," Bioconjugate Chem. 7: 144–149 (1996).(Issue No. 1).

Duncan, R., et al., "The role of polymer conjugates in the diagnosis and treatment of cancer," S.T.P. Pharma Sciences 6(4): 237–263 (1996). (Issue No. 4).

Duncan, Ruth, "Drug–polymer conjugates: potential for improved chemotherepy," Anti–Cancer Drugs #:175–210 (1992). (vol. 3).

Duncan, R., et al., "Anticancer agents coupled to N–(2–hydrozypropyl)methacrylamide copolymers. I. Evaluation of daunomycin and purmycin conjugates in vitro," Br. J. Cancer 55:165–174 (1987).

Fiebig, H.H., et al., "GB–21, a novel platinum polymer with antitumor activity in human renal and mammary xenografts," Proceedings of the American Association for Cancer Research 37:297 Abstract No. 2021 (1996). (Apr. 24, 1996).

Filipová–Vorpršálová, Marie, et al., "Biodistribution of trans–1,2–diaminocyclohexane–trimellito–platinum(II) attached to macromolecular carriers I. Poly (hydroxethyl–D, L–asparagine) carrier," Journal of Controlled Release 17: 89–98 (1991).

Fujii, K., et al. "Control of Pharmacokinetics and Nephrotoxicity of cis–DDP by Alginate," Proceed. Intern. Symp. Control. Rel. Bioact. Mater. 23: 639–640 (1996).

Han, Man Jung, et al., "Synthesis and Antitumor Activity of Polyanion–Pt–Complexes Containing Alicyclic Amines as Ligands," Journal of Bioactive and Compatible Polymers 9: 142–151 (1994). (Apr. 1994).

Johnsson, A., et al., "A topographic study on the distribution of cisplatin in xenografted tumors on nude mice," Anti–Cancer Drugs 7: 70–77 (1996).

Neuse, E.W., et al., "cis–Diaminedichloroplatinum(II) Complexes Reversibly Bound to Water–Soluble Polyaspartamide Carriers for Chemotherapeutic Applications. II: Platinum Coordination to Ethylenediamine Ligands Attached to Poly-(ethylene oxide)–Grafted Carrier Polymers," Journal of Inorganic and Organometallic Polymers 5(3): 195–207 (1995).

Schechter, B., et al., "Soluble Polymers as Carriers of Cis–Platinum," Journal of Controlled Release 10: 75–87 (1989).

Seymour, L.W., et al., "Effect of molecular weight ($M_w$) of N–(2–hydroxypropyl)mehtacrylamide copolymers on body distribution and rate of excretion after subcutaneous, intraperitoneal, and intravenous administration to rats," Journal of Biomedical Materials Research 21: 1341–1358 (1987).

Sohn, Youn Soo, et al., "Synthesis and antitumor activity of novel polyphosphazene–(diamine) platinum (II)," Int. J. Pharm 153:79–91 (1997).

Ranucci et al., "Poly(amidoamine)s with Potential as Drug Carriers: Degradation and Cellular Toxicity," *J. Biomaterial Science, Polymer Ed.,* 2(4), 303–315 (1991); *Chem. Abstr.,* 116, Abstr. No. 11092 (1992); only HCAPLUS version of Abstr. supplied.

Balázová, E. et al., "Antitumor Activity of Four Polymer Bound trans–1,2–diaminocyclohexaneplatinum (II)–4–carboxphtalate Complexes Tested in Different Model Systems," *Neoplasma.* 33:(06) 665–670 (1986).

Carraher, C.E. et al., "Polymeric Derivatives based on cis–Diamminedichloroplatinum (II) as Antineoplastic Agents," *Biological Activities of Polymer*. American Chemical Society. 221–231 (1982).

International Search Report for PCT Application No. PCT/US98/07659 (Oct. 30, 1998).

Ohya, Y. et al., "Synthesis and Cytotoxic Activity of Dextran–Immobilizing Platinum (II) Complex through Chelate–Type Coordination Bond," *Pure Appl. Chem.* A33(8) 1005–1016 (1996).

Neuse, E.W. et al., "Carrier Polymers for Cisplatin–type Anticancer Drug Models," *Polymers for Advanced Technologies*, John Wiley & Sons, Ltd. vol. 07, 867–872 (1996).

*Primary Examiner*—L. Eric Crane
*Attorney, Agent, or Firm*—Judy M. Mohr; Dehlinger & Associates

[57] ABSTRACT

A polymer-platinum compound for use in tumor treatment is described. The compound is composed of a biodegradable diamido-diamine polymer linked to a platinum species. The platinum species is released from the polymer to yield a platinum species having anti-tumor activity.

25 Claims, 9 Drawing Sheets

POLYMER-PLATINUM COMPOUNDS

This application claims the priority of U.S. provisional application Ser. No. 60/044,701, filed Apr. 18, 1997, which is incorporated herein by reference.

FIELD OF THE INVENTION

The present invention relates to a polymer-platinum compound for use in tumor treatment.

REFERENCES

Bogdanov, Jr., A. A., et al., *Bioconjugate Chem.* 7:144–149 (1996).

Filipová-Voprsǎlová, M., et al., *J. Controlled Release* 17 (89–98) (1991).

Freise, J., et al., *Arch. Int. Pharmacodyn.* 258:180–192 (1982).

Fuji, K., et al., *Proc. Intern. Symp. Control. Rel. Bioact. Mater.* 23:639–640 (1996).

Han, M. J., et al., *J. Bioact. and Biocompat. Polymers* 9:142 (1994).

Johnsson, A., and Cavallin-Ståhl, E., *Anti-Cancer Drugs* 7:70–77 (1996).

Neuse, E. W., et al., J. Inorganic and Organometallic Polymer 5(3):195–207 (1995).

Prestayko, A. W., CANCER AND CHEMO. VOL III (Crooke, et al., Eds.) Academic Press, N.Y., 133–154 (1981).

Schechter, B., et al., *J. Controlled Release* 10:75–87 (1989).

Steerenberg, P. A., et al, *International Journal of Pharmaceutics* 40:51–62 (1987).

Sur, B., et al, *Oncology* 40:372–376 (1983).

Weiss, R. B., et al., *Drugs* 46(3):360–377 (1993).

BACKGROUND OF THE INVENTION

Cis-diamminedichloroplatinum(II) (cisplatin) is widely used in cancer chemotherapy for treatment of solid tumors, including ovarian, testicular and head and neck, and is especially effective in the combined chemotherapy against squamous cell carcinoma and small cell lung carcinoma (Sur, et al., 1983; Steerenberg, et al., 1987).

Antitumor activity of cisplatin results from the ability of the diaquo species to crosslink the N-7 guanine residue of DNA producing intrastrand and interstrand crosslinks. To display antitumor activity, platinum complexes require two cis amine or ammine functionalities having at least one hydrogen atom that will hydrogen-bond to the oxygen atoms of the DNA phosphate groups and two strongly-bound leaving groups, e.g., chloride.

Like other cancer chemotherapeutic agents, cisplatin is a highly toxic drug. The main disadvantages of cisplatin are its extreme nephrotoxicity, which is the main dose-limiting factor, its rapid excretion via the kidneys, with a circulation half life of only a few minutes, and its strong affinity to plasma proteins (Freise, et al., 1982).

Attempts to minimize the toxicity of the drug have included combination chemotherapy, synthesis of cisplatin analogues (Prestayko, 1991; Weiss, et al., 1993), immunotherapy and entrapment in liposomes (Sur, et al., 1983; Weiss, et al., 1993) and preparation of polymer-platinate conjugates (Bogdanov, et al., 1996; Filipová-Voprsǎlová, et al., 1991; Fuji, et al., 1996; Han, et al., 1994; Johnsson and Cavallin-Ståhl, 1996; Neuse, et al., 1995; Schechter, et al., 1989).

With respect to the synthesis of cisplatin analogues, numerous platinum analogues have undergone preclinical and clinical trials, however only cisplatin and carboplatin have been approved for routine clinical use. Many of the analogues show no significant improvement in therapeutic index when compared to cisplatin. Cisplatin and its analogues have other drawbacks. Many are inactive when administered orally, some have low solubility in water and most induce severe toxic side effects including renal disfunction, nausea and vomiting, myelosuppression and neurotoxicity.

With respect to the preparation of polymer-platinum conjugates, such conjugates have been proposed as an approach to increasing solubility and reducing systemic toxicity. Although several platinum-polymer systems have been reported (Bogdanov, et al., 1996; Filipová-Voprsǎlová, et al., 1991; Fuji, et al., 1996; Han, et al., 1994; Johnsson and Cavallin-Ståhl, 1996; Neuse, et al., 1995; Schechter, et al., 1989) few have successfully entered clinical investigation and few have displayed significant benefit in vivo. Failure has been due to lack of biocompatibility, toxicity of the proposed carrier, lack of antitumor activity and/or other problems.

SUMMARY OF THE INVENTION

Accordingly, it is an object of the invention to provide a polymer-platinum compound having antitumor activity in vivo.

In one aspect, the invention includes a pharmaceutical composition for use in tumor treatment, comprising a polymer-platinum compound composed of a biodegradable, water-soluble, diamido-diamine polymer and a platinum species linked to the polymer. The platinum species is released from the polymer under physiological conditions to yield a platinum species which has, or is converted in vivo to have, anti-tumor activity, as evidenced by the anti-tumor activity of the polymer-platinum compound when administered to a tumor-bearing mammal.

In one embodiment, the platinum species is linked to a carboxyl group in the polymer. In another embodiment, the platinum species is linked by hydrogen bonds to a functionalized polycyclic oligosaccharide which is itself linked to the polymer.

The diamidodiamine polymer, in one embodiment, has the backbone structure:

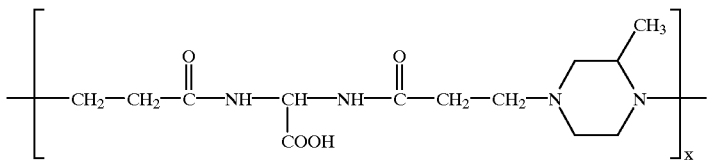

In another embodiment, the polymer has the backbone structure:

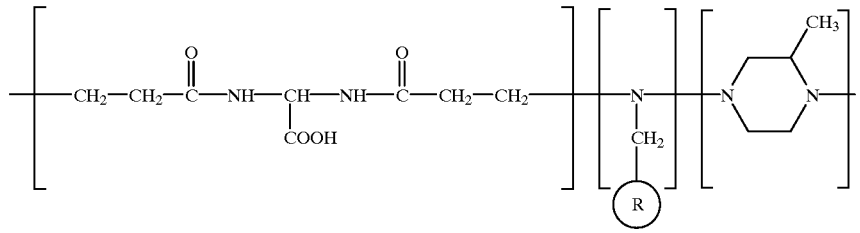

wherein R is a polycyclic oligosaccharide.

In another embodiment, the polymer has the backbone structure:

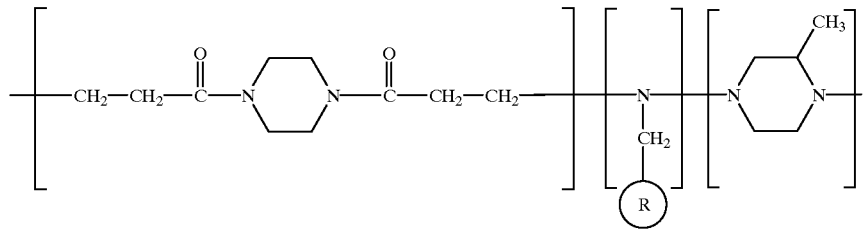

wherein R is a polycyclic oligosaccharide.

The polymer-platinum compound is dissolved in an aqueous medium suitable for parenteral administration.

In another aspect, the invention includes a method of targeting platinum to a solid tumor in a subject. The method includes preparing a polymer-platinum compound composed of a platinum species and a water-soluble, biodegradable diamido-diamine polymer. The platinum species is bound to the polymer for release therefrom under physiological conditions to yield a platinum species which has, or is converted in vivo to have, anti-tumor activity. The compound is administered in a pharmaceutically effective amount to the subject.

These and other objects and features of the invention will be more fully appreciated when the following detailed description of the invention is read in conjunction with the accompanying drawings.

DETAILED DESCRIPTION OF THE INVENTION

I. Preparation of the Polymer-platinum Compound

1. Diamidodiamine Polymer Preparation

Figure 1A:
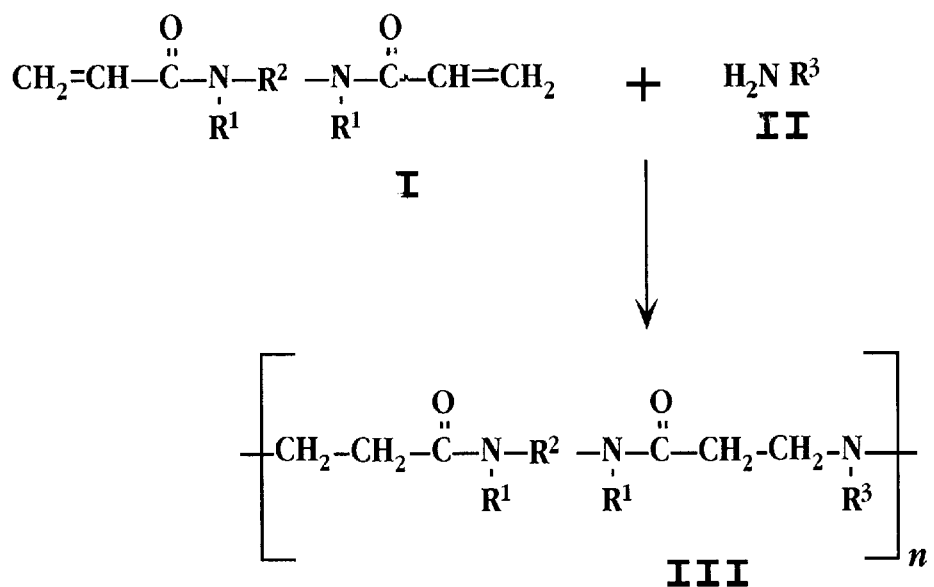
FIGS. 1A–1B show general reaction schemes for synthesis of polyamidoamine polymers by hydrogen-transfer polyaddition of a primary amine (FIG. 1A) or a secondary amine (FIG. 1B) to a bisacrylamide.
Figure 1B:
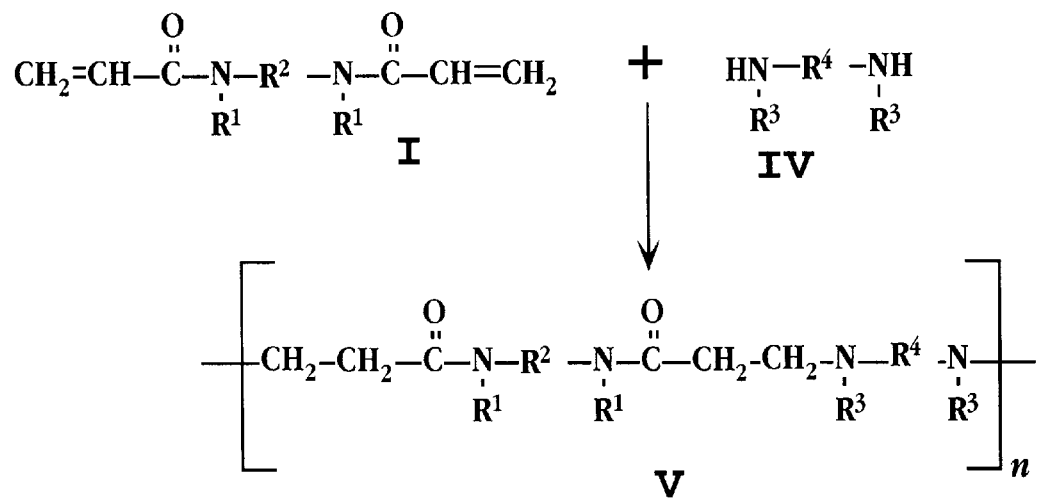

The diamidodiamine polymers of the present invention are obtained by hydrogen-transfer polyaddition of primary or secondary amines to bisacrylamides in a proton-donor solvent, such as water. General reaction schemes are illustrated in FIGS. 1A–1B, where in FIG. 1A a bisacrylamide (Compound I) is reacted with a primary amine (Compound II) to yield a polydiamidodiamine polymer (Compound III). In FIG. 1B, a secondary amine (Compound IV) is reacted with a bisacrylamide (Compound I) to obtain a polyamidoamine polymer (Compound V).

The "R" groups in the compounds shown in FIGS. 1A–1B are typically any pendant group suitable for attaching platinum and which does not adversely effect the in vivo solubility or toxicity properties of the polymer-platinum complex. Exemplary groups include alkyl, lower alkyl, peptidyl groups, and polycyclic oligosaccharides. "Alkyl" refers to hydrocarbon chains, typically ranging about 1 to 12 carbon atoms in length. The hydrocarbon chains may be saturated or unsaturated and may optionally contain additional functional groups attached thereto, such as carboxyl, amide, hydroxyl or halo. The hydrocarbon chains may be branched or straight chain. Exemplary alkyl groups include ethyl, propyl, 1-methylbutyl, 1-ethylpropyl and 3-methylpentyl.

"Lower alkyl" refers to an alkyl group containing from 1 to 5 carbon atoms, and may be straight chain or branched, as exemplified by methyl, ethyl, n-butyl, i-butyl, t-butyl, including fluorinated, monohydroxy, or chlorinated forms thereof.

"Peptidyl" or "amino acid" refers to any compound containing both an amino group and a carboxylic acid group. The amino group may occur at the position adjacent to the carboxy function, such as in the α-amino acids, or at any location within the molecule. The amino acid may also contain additional functional groups, such as amino, thio, carboxyl, carboxamide, imidazole, etc. The amino acid may be synthetic or naturally occurring. Representative peptidyl spacer moieties include amino acid combinations of Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly, Gly-Phe-Phe-Leu, Gly-Leu-Leu-Gly, Gly-Phe-Tyr-Ala, Gly-Phe-Gly-Phe, Ala-Gly-Val-Phe, Gly-Phe-Phe-Gly, Gly-Phe-Leu-Gly-Phe, Gly-Gly-Phe-Leu-Gly-Phe. Preferred spacer moieties are Gly-Gly and Gly-Phe-Leu-Gly.

With continuing reference to FIGS. 1A–1B, the "R" pendant groups, described above, preferably attach to platinum through a charged functionality, such as carboxyl, amide or amine. Alkyl or lower alkyl pendant groups are preferably modified accordingly to include such a charged functionality. Where the pendant group is a peptidyl group, the platinum compound can be complexed to the peptide or to a proximal end group covalently attached to the peptide. For example, a diamine, such as ethylenediamine, or a carboxyl function, such as a malonyl, can be attached to the end of the peptide for attachment of the platinum.

Figure 2:
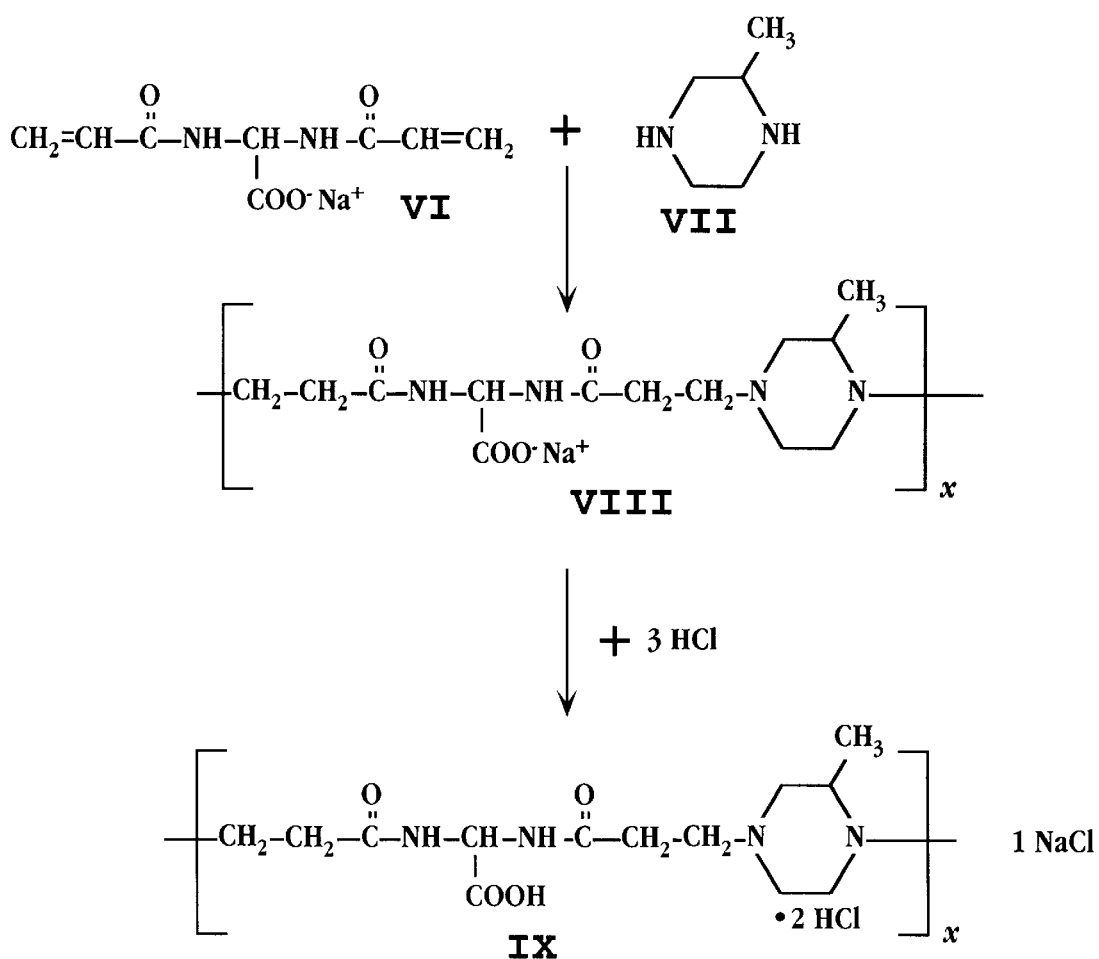
FIG. 2 is a reaction scheme for synthesis of a first exemplary polyamidoamine, poly(diamidocarboxy-piperazinyl) (PACP)

Preparation of an exemplary diamidodiamine polymer, poly(bisacrylamido-acetoxy-piperazinyl) (PACP), is described in Example 1 and illustrated in FIG. 2. 2,2'-bis (acrylamido) acetic acid sodium salt (Compound VI) was dissolved in water and cooled to 10° C. 2-methyl piperazine (Compound VII) was added to the solution of bis (acrylamido) acetic acid and maintained at 25° C. for five days. The reaction mixture was then acidified to pH=3 with hydrochloric acid to yield poly(bisacrylamido-acetoxypiperazinyl) (Compound IX), referred to herein as "PACP". PACP is a polydiamidocarboxypiperazinyl polymer, indicative of a polymer in which the diamino portion of the subunit is cyclic, that is, where the diamino portion of the polymer is a piperazine, and more specifically, 2-methylpiperazine.

Figure 3:
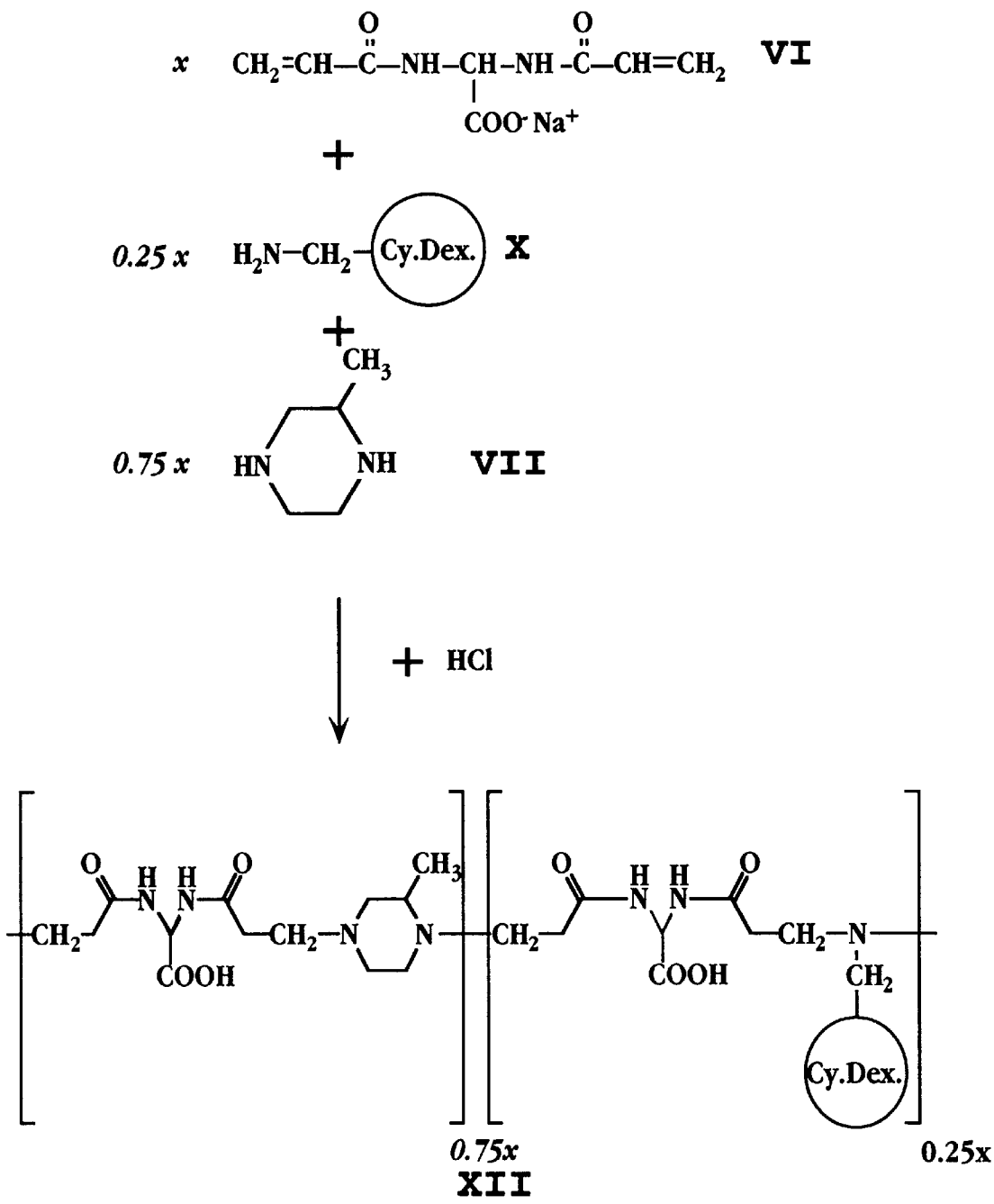
FIG. 3 is a reaction scheme for synthesis of a second exemplary polyamidoamine, poly(diamidocarboxy-aminocyclo dextrin-piperazinyl) (PACP-cyc)

Preparation of a second exemplary polydiamidodiamine polymer is described in Example 2 and illustrated in FIG. 3. As in preparation of PACP, 2,2'-bis(acrylamido) acetic acid sodium salt (Compound VI) was dissolved in water and cooled. Aminomethyl-β-cyclodextrin (Compound X) and 2-methyl-piperazine (Compound VII) were added and reacted. The mixture was acidified with hydrochloric acid to give a second general subclass, poly(diamidocarboxy-aminocyclohextrinpiperazinyl), or more specifically poly (bisacrylamido-acetoxy-aminoCy.dex-piperazinyl) (Compound XII). This polymer is referred to herein as "PACP-cyc".

Figure 4:
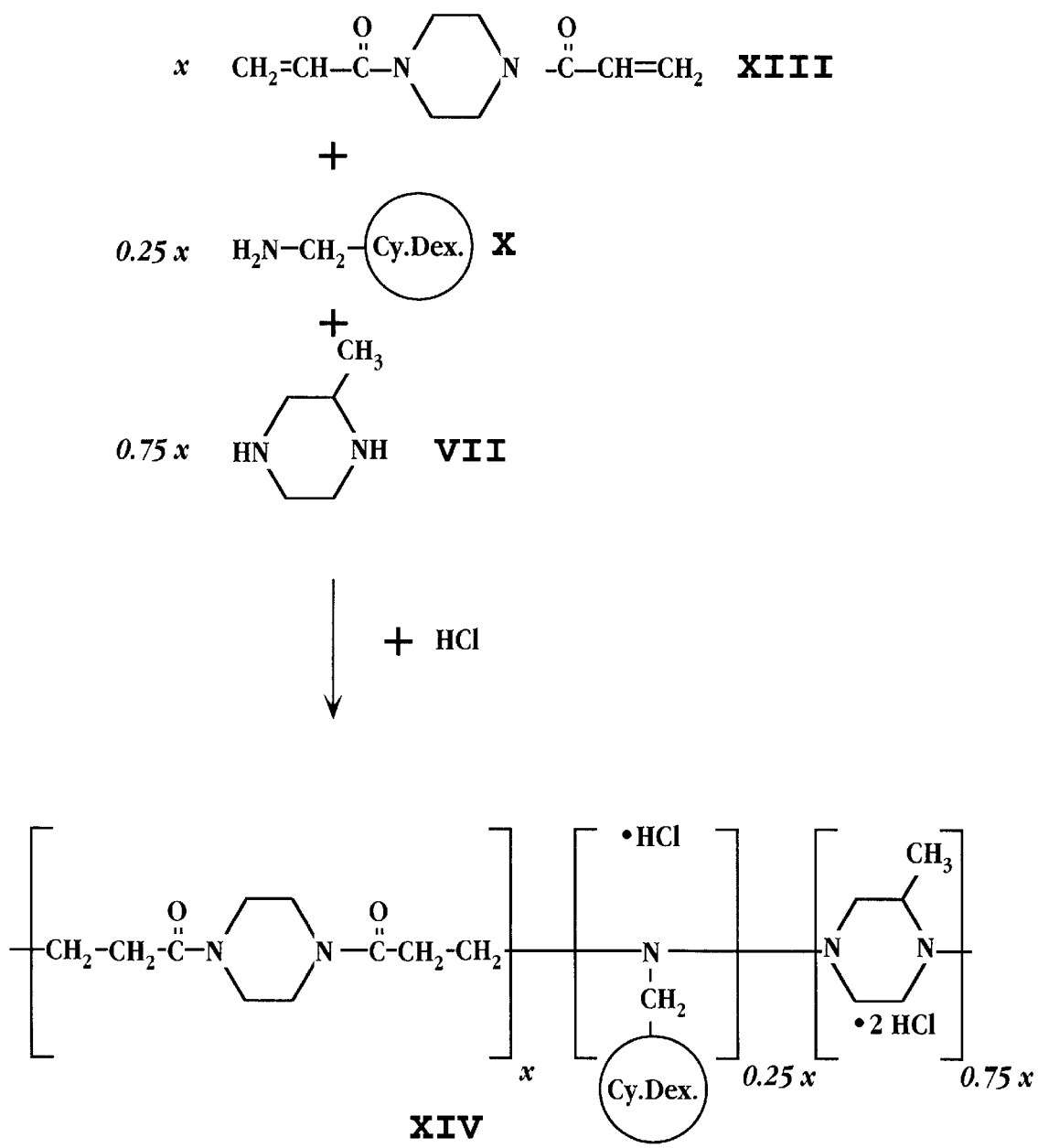
FIG. 4 is a reaction scheme for synthesis of a third exemplary polyamidoamine, poly[(bisacryloyl piperazine)-aminocyclodextrin-piperazinyl] (PAP-cyc)

Preparation of a third exemplary polymer is described in Example 3 and illustrated in FIG. 4.

Here, the bisacrylamide 1,4-bis(acryloyl) piperazine (Compound XIII) was reacted as described above with aminomethyl-β-cyclodextrin (Compound X) and 2-methyl-piperazine (Compound VII) to form polyl[(bisacryloyl piperazine)-aminocyclodextrin-piperazinyl] (Compound XIV), referred to herein as "PAP-cyc".

As will be described below, the polydiamidodiamine polymer are reacted with platinum to prepare polymer-platinum compounds. As referred to herein, "platinum" or "platinum species", typically used in the context of a platinum complex or compound, refer to a platinum metal atom bound to one or more ligands. The platinum atom may carry a formal charge, such as in the case of platinum salts such as $K_2PtCl_4$, potassium tetrachloroplatinate, in which the platinum carries a formal charge of (−2), or may carry no formal charge, as in cisplatin, $PtCl_2(NH_3)_2$. The platinum metal atom may exist in various oxidation states, such as Pt(0), Pt(II), or Pt(IV), although platinum, in the context of the present invention, is typically Pt(II). The platinum species can be in any coordination state, but is typically four-coordinate.

"Platinate" or "platinate species", as used herein, refers to a platinum compound in which the platinum atom is in an oxidation state of Pt(II) or Pt(IV).

The polydiamidodiamine polymers have moieties or are derivatized to include moieties for binding with platinum. Moieties suitable for binding platinum are ones which bind platinum via bonds that are preferably stable in vitro, but can be cleaved in vivo to release the active form of the platinum compound. For example, PACP-cyc and PAP-cyc include a polycyclic oligosaccharide, cyclodextrin, for binding the platinum species. It will be appreciated that the oligosaccharide can be derivatized to provide additional functional groups for binding with the platinum species.

The polymer PACP includes a free hydroxyl or carboxyl through which the platinum species can bind. More generally, the polymers can be derivatized to include a peptidyl, alkyl or lower alkyl pendant moiety linked to the polyamidoamine backbone, by techniques known to those of skill in the art. It is also envisioned that the platinum could be complexed to the polymer through the acidic nitrogens or a variety of platinum chelating functionalities that have been added to the polymer backbone.

After the polymerization reaction was complete for each of the polymers described in Examples 1–3, the product was isolated by diluting with water, acidifying with hydrochloric acid, ultrafiltering through a membrane with a cut-off of 3,000 daltons, and lyophilizing the retained fraction.

Polymers having a molecular weight in the range of 1,000–5,000,000 daltons are suitable for use in the present invention, with a range between 10,000–30,000 daltons preferred. Because the polyamidoamine polymers are biodegradable along the polymer backbone, particularly at the N-C linkages in the presence of peptidase enzymes, a wide range of molecular weight is suitable for administration in vivo.

2. Preparation of Polymer-platinum Compound

Figure 5:
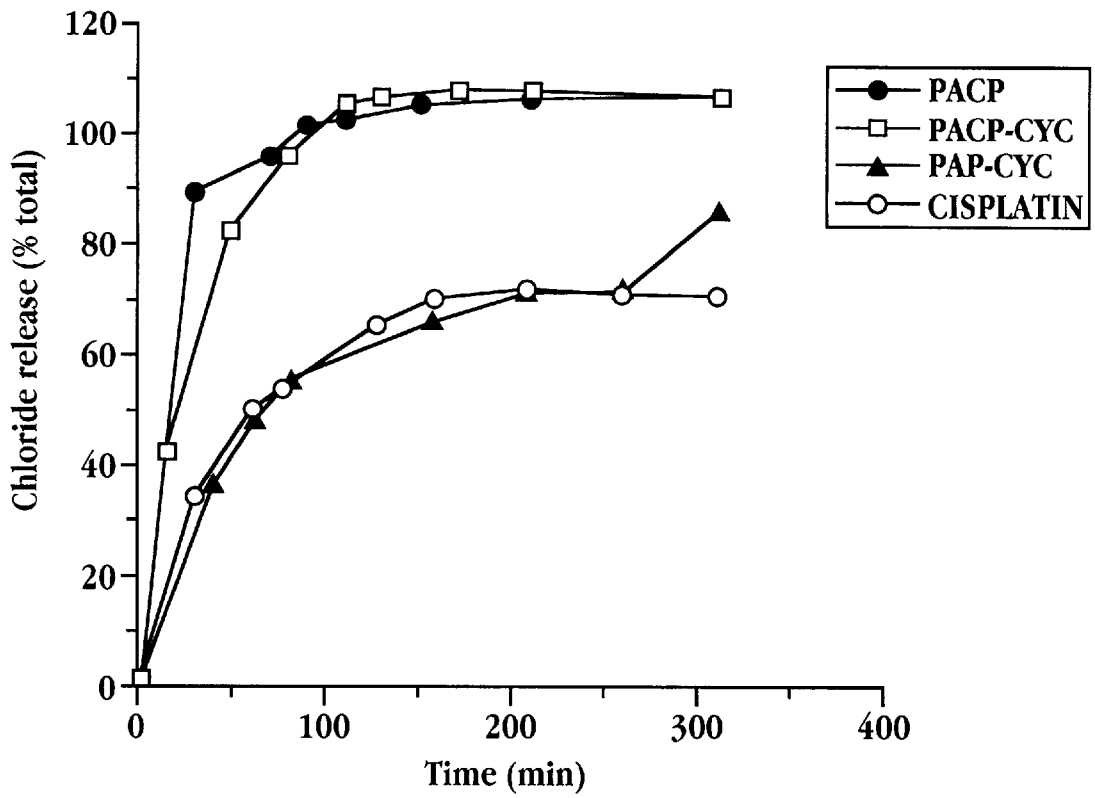
FIG. 5 is a plot showing the kinetics of chloride release during reaction of cisplatin with the diamidodiamine polymers, where the percent of chloride released as a function of time is shown for PACP (closed circles), PAP-cyc (open squares), PACP-cyc (closed triangles) and cisplatin (open circles)

The polymer-platinum compound was prepared by adding a solution of the desired polymer dropwise over about 15 minutes to a stirring solution of cisplatin in double distilled water. The mixture was stirred at room temperature (25–27° C.) for 1–2 hours longer than required for the reaction to go to completion, as determined by monitoring the release of chloride ion using a Jenway PCLM3 chloride meter containing a silver electrode. FIG. 5 shows the kinetics of chloride release during reaction of cisplatin with the diamidodiamine polymers PACP (closed circles), PAP-cyc (closed squares) and PACP-cyc (closed triangles). The higher rate of chloride release during reaction with PACP and PAP-cyc suggests more rapid coordination with these polymers than with PACP-cyc which has a chloride release rate approximately that of cisplatin (open circles).

Following completion of the polymer-platinum reaction, the mixtures were dialysized against double distilled water followed by freeze-drying to yield the polymer-platinum compounds.

The polymer-platinum compounds described above were prepared using cisplatin as the starting material for platinum, as described in Example 4. It will be appreciated that any of a number of readily available or synthesized platinum complexes can be utilized to form the polymer-platinum complex of the present invention. The platinum starting material should possess at least one readily displacable ligand, preferably two, for complexing with the polymer-spacer, and is preferably water soluble, for ease of synthesis. The starting platinum compound does not necessarily have therapeutic activity in vivo, and is preferably converted in vivo to a biologically active form upon biologically-induced displacement of the polymer-spacer ligands at the intended target site.

The polymer-platinum compounds were characterized by estimating the weight average molecular weight (Mw) and number average molecular weights (Mn) by gel permeation chromatography. The polymer-platinum compounds were also analyzed for platinum content by two methods, o-Phenylenediamine Colorimetric Assay (o-PDA) and atomic absorption spectroscopy (AAS). These methods are described in the Methods section below. Table 1 summarizes the platinum content in weight percent for PACP, PACP-cyc and PAP-cyc.

TABLE 1

Platinum Content of the Polymer-Platinum Compounds

| Polymer | Pt Loading (% wt) | |
|---|---|---|
| | o-PDA[1] | AAS[2] |
| PACP | 15 | 10 |
| PAP-cyc | 69 | 53 |
| PACP-cyc | 60 | 56 |

[1] o-phenylenediamine colorimetric assay
[2] Atomic absorption spectroscopy

The polyamidoamine polymers have one or more sites for coordinating with platinum, as demonstrated in the exemplary polymers. Platinum binding to PACP-cyc and PAP-cyc is primarily via the functionalized polycyclic oligosaccharide, which is itself linked to the polymer. The high platinum content, 50–60 wt % (Table 2), in these polymers suggests that the polycyclic oligosaccharide cyclodextrin readily captures the platinum species.

II. In vitro Characterization

1. Cytotoxicity of PACP

The in vitro cytotoxicity of PACP was evaluated according to the procedure described in Example 5. The polymer was added to cultures of L132 or B16 melanoma cells and incubated for 72 hours. After incubation, 5-dimethylthiazol-2-yl-2,5-diphenyl tetrazolium bromide (MTT) was added to the culture medium and incubated before removal of the culture medium and addition of dimethylsulfoxide to dissolve the MTT crystals. The absorbance of the cells was determined to compare the viability of the test cultures to a control culture of cells in the absence of polymer. As a positive control, poly-L-lysine was tested and for comparison, the natural polymer dextran was tested.

Figure 6:
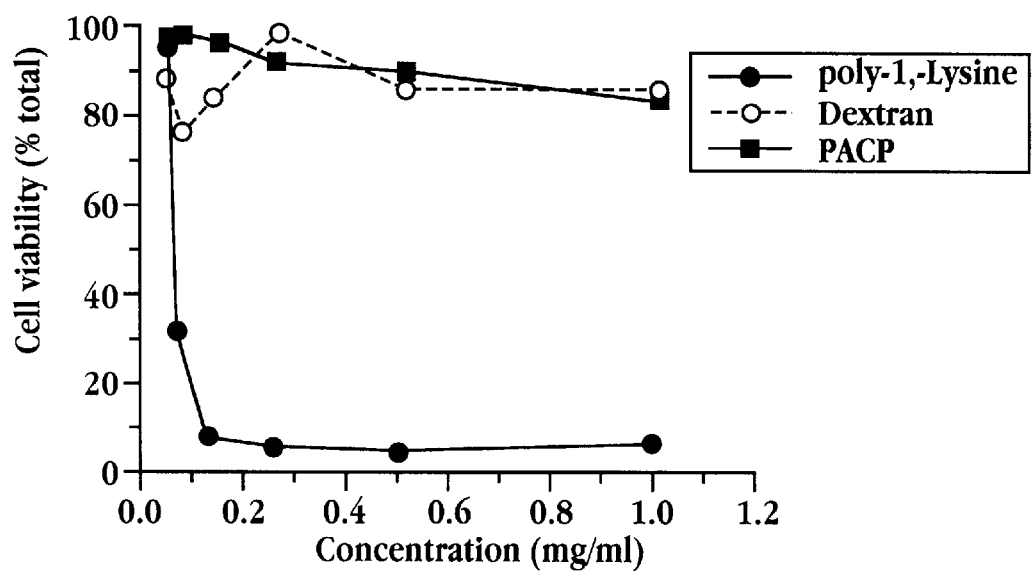
FIG. 6 is a plot showing cell viability, expressed as a percentage of a control of untreated cells, as a function of polymer concentration, in mg/ml, for poly-L-lysine (closed circles), dextran (open circles) and PACP (closed squares)

The results are shown in FIG. 6, where cell viability, expressed as a percentage of a control of untreated cells, is plotted against polymer concentration, in mg/ml, for poly-L-lysine (closed circles), dextran (open circles) and PACP (closed squares). As seen in the figure, PACP is non-toxic to the cells, as evidenced by the cell viability of greater than 90% over the 0.05–1.0 mg/ml polymer concentration range tested. In contrast, poly-L-lysine was cytotoxic, with few cells surviving at a polymer concentration of greater than 0.1 mg/ml.

The biocompatibiity of PACP also was evaluated in vivo by administering the neat polymer to mice and monitoring the body weight as a function of time. These data (not shown) indicate that the polymer is non-toxic to the animals, as evidenced by their continuing weight gain as a function of time.

2. Release Rate of Platinum

As described in Example 6, the polyamidoamine-platinum compounds prepared as described above were tested in vitro for release of platinum. The in vitro release was determined at pH 5.5 and at pH 7.4 by dissolving the test polymers in citrate phosphate buffer or in phosphate buffered saline (PBS), respectively. The free Pt in the buffer was analyzed using the o-PDA assay or by atomic absorption spectroscopy as described in the Methods section below.

Figure 7A:
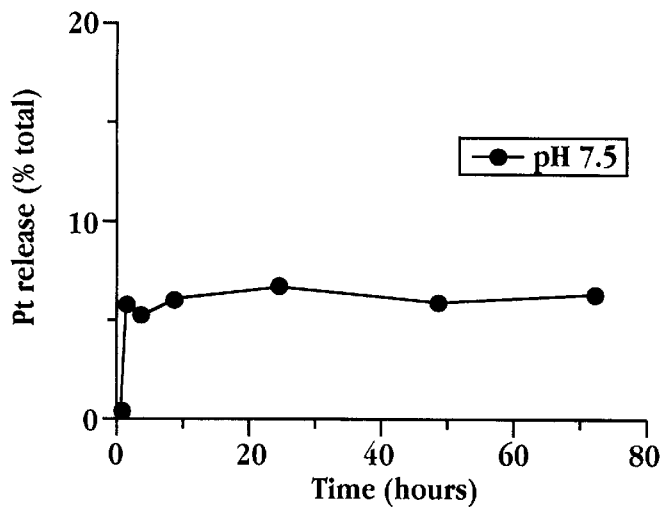
FIG. 7A–7C are plots showing the percentage of platinum released from polyamidoamine-platinum compounds at pH 5.5 (open circles) and at pH 7.4 (closed circles) as a function of time, for PACP-Pt (FIG. 7A), PACP-cyc-Pt (FIG. 7B) and PAP-cyc-Pt (FIG. 7C)
Figure 7B:
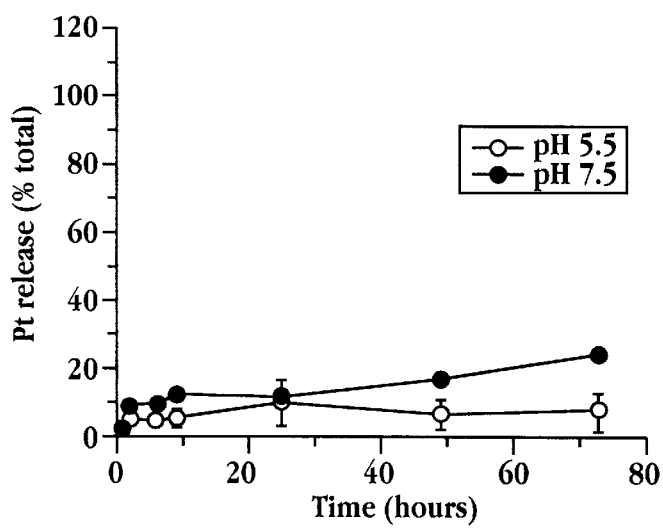
Figure 7C:
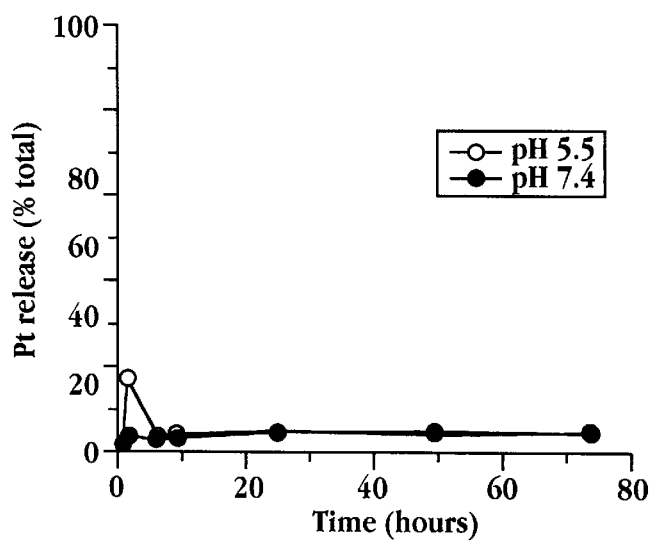

The results are shown in FIGS. 7A–7C, where the concentration of Pt released from the polyamidoamine-platinum compounds, expressed as a percentage of the total available, is plotted as a function of time. FIG. 7A shows the platinum release rate for polyamidoamine PACP-Pt at pH 7.4. After an initial release of about 6% of the total platinum in the first hour, no more platinum was released. For the PACP-cyc-Pt compound, shown in FIG. 7B, the release of platinum at pH=7.4 (closed circles) slowly increased over the 75 hour test, with about 25% of the total platinum released. The release of platinum from PACP-cyc-Pt at pH=5.5 (open circles) was lower than at pH=7.4 with less than about 10% of the total platinum released. The release of platinum from PAP-cyc-Pt compound is shown in FIG. 7C, where at both pH 5.5 (open circles) and pH 7.4 (closed circles) the release of platinum was less than 10%.

The in vitro release data indicate that the platinum species in the polyamidoamine-platinum compounds is strongly held, which is advantageous for product stability. As will be seen below, when administered in vivo the compounds release platinum at a rate sufficient for anti-tumor activity, perhaps at a rate different from that in vitro due, at least in part, to the biodegradable backbone of the polyamidoamine.

3. Cytotoxicity of Polyamidoamine-Platinum Compounds

The in vitro cytotoxicity of the polyamidoamine-platinum compounds was evaluated using the MTT assay described above and in Example 5. The cytotoxicity of the compounds, and of free cisplatin, towards the lung cell lines, L132, COR-L23 and H69, was determined, as set forth in Example 7.

Figure 8A:
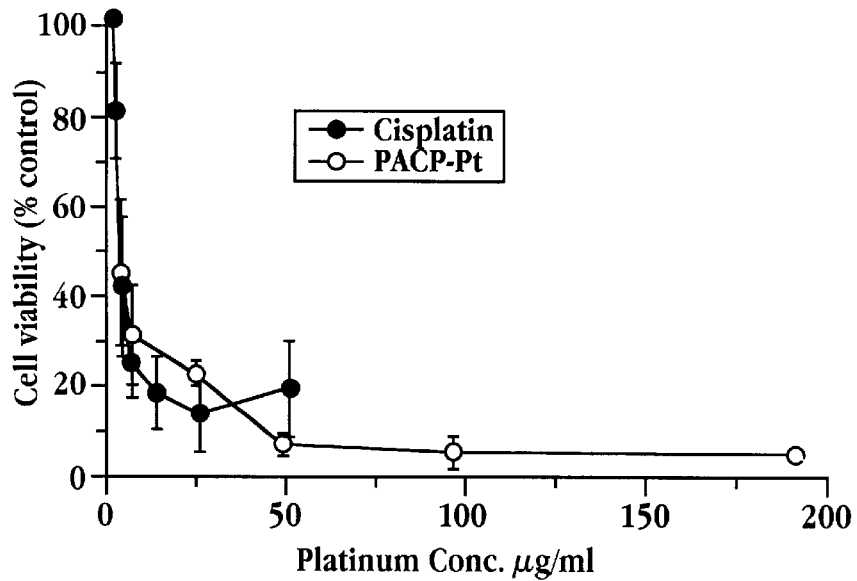
FIG. 8A is a plot showing the effect of diamidodiamine PACP-Pt against L132 cells in vitro, expressed as percent cell viability relative to a control of untreated cells as a function of platinum concentration in μg/ml, for PACP-Pt (open circles) and cisplatin (closed circles)

FIG. 8A shows the effect of PACP-Pt on L132 cells (open circles), where the cell viability, expressed as a percentage of untreated, control cells, is plotted against platinum concentration. For comparison, the cell viability for cisplatin is shown (closed circles). The profiles of PACP-Pt and of cisplatin are similar, indicating approximately equal potency when tested against this cell line in vitro.

Figure 8B:
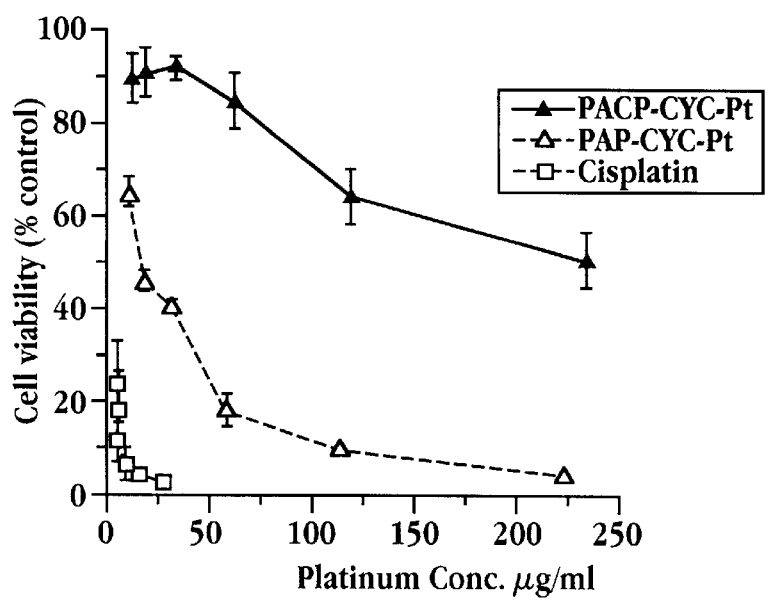
FIG. 8B is a plot showing the effect of diamidodiamine-Pt compounds against L132 cells in vitro, expressed as percent cell viability relative to a control of untreated cells as a function of platinum concentration in μg/ml, for PAP-cyc-Pt (closed triangles) and PACP-cyc-Pt (open triangles) and for cisplatin (open squares)

FIG. 8B shows the results for the polyamidoamine-Pt compounds PAP-cyc-Pt (closed triangles) and PACP-cyc-Pt (open triangles) and for cisplatin (open squares). The polyamidoamine-Pt compounds are less potent than cisplatin, in particular PAP-cyc-Pt where cell viability was greater than about 60% up to a platinum concentration of 225 µg/ml.

Figure 9A:
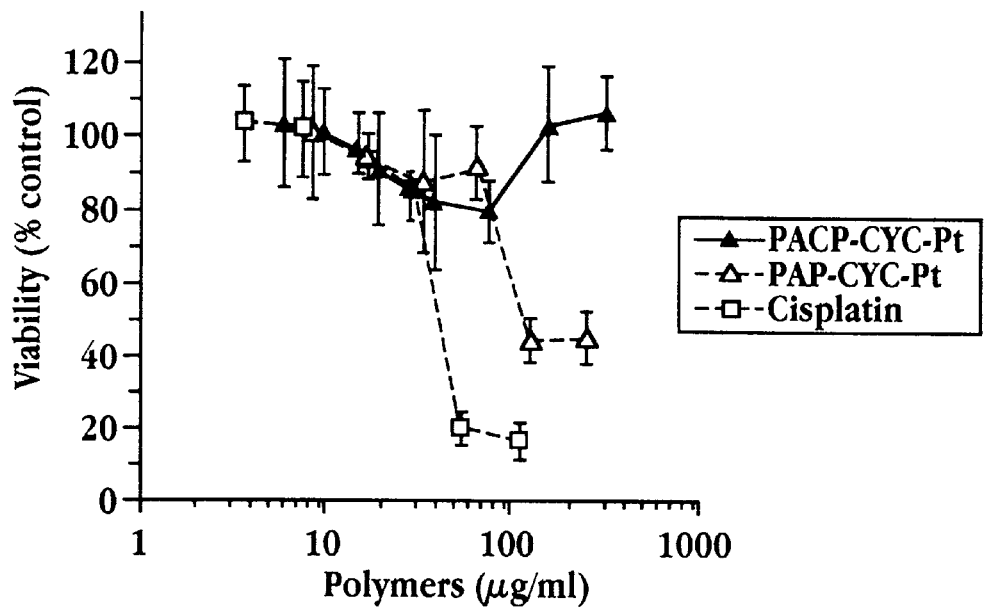
FIG. 9A is a plot showing the effect of diamidodiamine-Pt compounds against H69 small cell lung carcinoma cells in vitro, expressed as percent cell viability relative to a control of untreated cells as a function of polymer concentration in μg/ml, for PAP-cyc-Pt (closed triangles), PACP-cyc-Pt (open triangles) and for cisplatin (open squares)
Figure 9B:
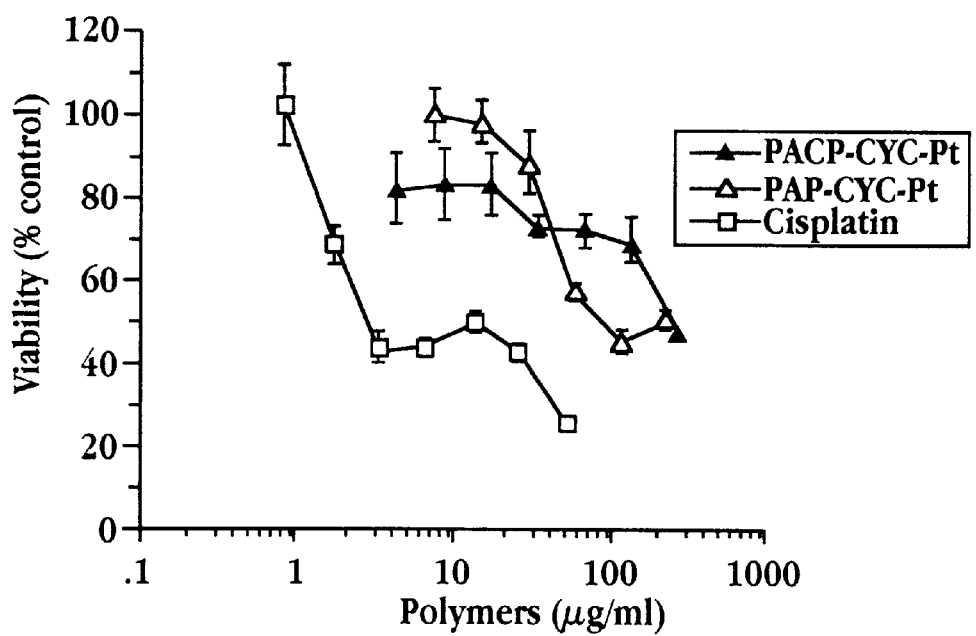
FIG. 9B is a plot showing the effect of diamidodiamine-Pt compounds against COR-L23 cells in vitro, expressed as percent cell viability relative to a control of untreated cells as a function of polymer concentration in μg/ml, for PAP-cyc-Pt (closed triangles), PACP-cyc-Pt (open triangles) and for cisplatin (open squares)

FIGS. 9A and 9B shows cell viability as a function of polymer concentration for the polyamidoamine-Pt compounds PAP-cyc-Pt (closed triangles) and PACP-cyc-Pt (open triangles) for a small cell lung carcinoma H69 cell line (FIG. 9A) and for COR-L23 cell (FIG. 9B), compared to cisplatin (open squares). The cyclic polyamidoamine-Pt compounds exhibit less potency to both cell lines than cisplatin.

The in vitro potency of the polyamidoamine-Pt compounds is summarized in Table 2 where the concentration of polyamidoamine-platinum compound required to produce a 50% decrease in cell viability ($IC_{50}$, µg/ml) was calculated from the data presented above.

TABLE 2

Summary of In vitro Potency

| Compound | $IC_{50}$ µg/ml | | |
|---|---|---|---|
| | L132 | COR-L23 | H-69 |
| Cisplatin | 4.80 ± 1.29 | 7.38 ± 2.78 | 45.9 ± 20 |
| PACP-Pt | 4.9 | — | — |
| PAP-cyc-Pt | 120.0 | 241.2 | 174.7 |
| PACP-cyc-Pt | 10.8 | 88.0 | 66.6 |

Although the polymer-platinum compounds exhibit lower in vitro potency than the platinum species cisplatin, the decrease in potency is offset by improvements in toxicity and therapeutic efficacy in vivo, as will be seen below.

III. In vivo Characterization of Polyamidoamine-Platinum Compounds

The polyamidoamine-platinum compounds prepared as described above were tested in vivo in mice to evaluate anti-tumor activity and toxicity using an L1210 intraperitoneal tumor model and a B16 melanoma intraperitoneal tumor model.

1. L1210 Tumor Inoculated Intraperitoneally

As described in Example 8, the polyamidoamine-platinum compounds PACP-Pt and PAP-cyc-Pt were tested against an L1210 intraperitoneal (i.p.) tumor model. The tumor was inoculated on day 0 and followed by treatment on days 1, 2 and 3 with neat PACP, PACP-Pt or PAP-cyc-Pt administered intraperitoneally. Free cisplatin was administered as a comparative treatment. The results are tabulated in Table 3.

The data in Table 3 is expressed as the ratio of the mean survival time of treated animals to the mean survival time of the untreated control animals×100 (T/C). Cisplatin was administered at platinum doses of 2 mg/kg and 3 mg/kg. PAP-cyc-Pt was administered at platinum doses of 3 mg/kg and 5 mg/kg. PACP-Pt was administered at platinum dosages of 3 and 5 mg/kg and PACP alone was administered at 90 mg/kg.

TABLE 3

| Treatment | Dose Pt (mg/kg) | T/C | Toxic Deaths |
|---|---|---|---|
| Cisplatin | 2 | 171 | 0/10 |
| | 3 | 64 | 9/10 |
| PAP-cyc-Pt | 3 | 172 | 0/5 |
| | 5 | 76 | 3/5 |
| PACP-Pt | 3 | 170 | 0/5 |
| | 5 | 127 | 5/10 |
| PACP | 90 mg/kg polymer alone | 95 | 0/5 |

Figure 10:
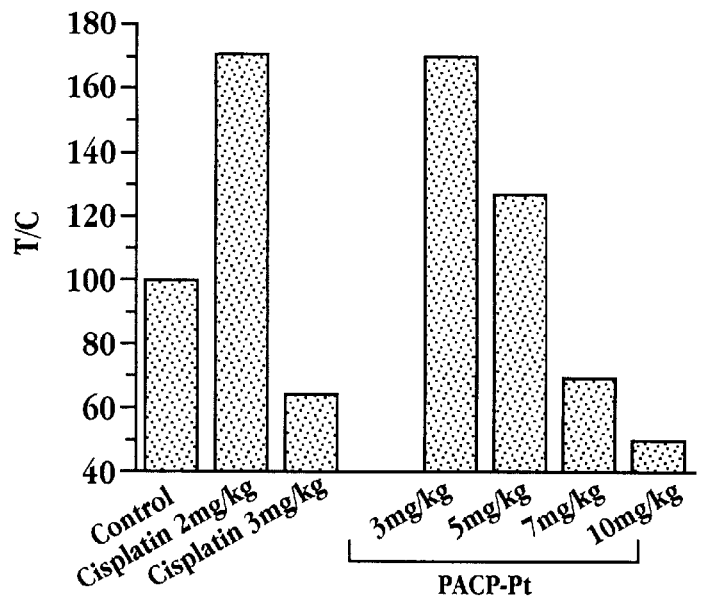
FIG. 10 is a bar graph showing the effect of PACP-Pt against an i.p. L1210 tumor model, expressed as the ratio of the mean survival time of treated animals to the mean survival time of the untreated control animals×100 (T/C) for platinum dosages of 3, 5, 7, and 10 mg/kg and compared to animals receiving 2 or 3 mg/kg cisplatin and to untreated, control animals.

The data presented in Table 3 for PACP-Pt is shown graphically in FIG. 10. The data shows that platinum complexed to the polyamidoamine polymer decreases the toxicity relative to cisplatin, without reducing efficacy, as evidenced by comparing the T/C values (efficacy) and toxic deaths (toxicity) at dosages of 3 mg/kg for the polymer-platinum compounds and cisplatin. These results, and in particular the fact that no reduction in therapeutic efficacy was observed in vivo, are of particular interest, and in fact, quite surprising, in view of the lower potency observed in vitro.

2. Intraperitoneal B16 Melanoma Tumor Model

As described in Example 8, the polyamidoamine-platinum compound PAP-cyc-Pt was tested against a B16 melanoma model inoculated intraperitoneally (i.p.). On the day after inoculation, PAP-cyc-Pt was administered i.p. as a single dose at platinum concentrations of 5, 10, 15 mg/kg. Free cisplatin was administered at dosages of 5 and 10 mg/kg for comparison. The results are tabulated in Table 4.

TABLE 4

| Treatment  | Dose Pt (mg/kg) | T/C | Toxic Deaths |
|------------|-----------------|-----|--------------|
| Cisplatin  | 5               | 134 | 0/5          |
|            | 10              | 78  | 3/5          |
| PAP-cyc-Pt | 5               | 119 | 0/5          |
|            | 10              | 114 | 0/5          |
|            | 15              | 92  | 2/5          |

The data shows that platinum administered in the form of polyamidoamine-Pt compound improves the therapeutic window by decreasing the toxicity of the platinum. Cisplatin administered at a dose of 10 mg/kg platinum, resulted in 3/5 toxic deaths with a T/C value of 78. In contrast, a 10 mg/kg dose of platinum administered in the form of polyamidoamine-Pt had no toxic deaths (0/5) and a T/C value of 114. As noted above for the L1210 tumor model, the observed improvement in therapeutic efficacy, as evidenced by the T/C values, for the polymer-platinum compounds is surprising in view of the in vitro result which indicated a loss of potency for the polymer-platinum compounds.

Figure 11:
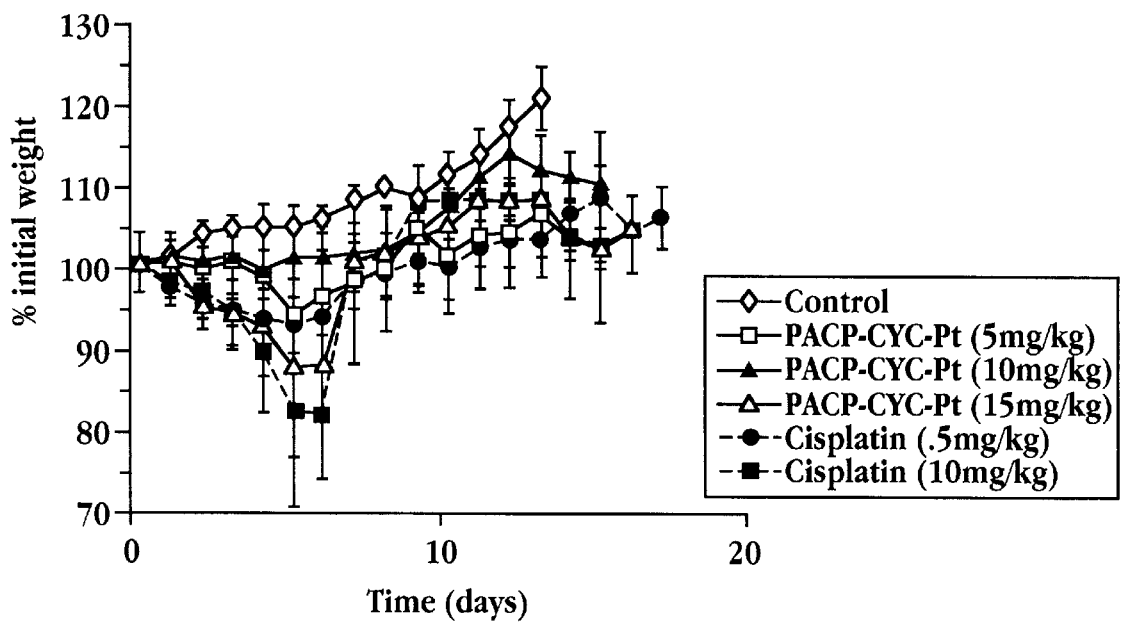
FIG. 11 is a plot showing the effect of the PAP-cyc-Pt compound on the body weight of mice bearing a B16 melanoma inoculated intraperitoneally, expressed as a percentage of initial weight against time, in days, for tumor-bearing mice treated with PAP-cyc-Pt at platinum dosages of 5 mg/kg (open squares), 10 mg/kg (closed triangles) and 15 mg/kg (open triangles), mice treated with cisplatin at 5 mg/kg (closed circles) and 10 mg/kg (closed squares) and for untreated mice (open diamonds).

FIG. 11 shows the effect on the body weight of C57B1/6J mice treated with PAP-cyc-Pt and compared to C57B1/6J mice treated with cisplatin. The data are expressed as a percentage of initial weight against time, in days, for tumor-bearing mice treated with PAP-cyc-Pt at platinum dosages of 5 mg/kg (open squares), 10 mg/kg (closed triangles) and 15 mg/kg (open triangles), mice treated with cisplatin at 5 mg/kg (closed circles) and 10 mg/kg (closed squares) and for untreated mice (open diamonds). Mice treated with the 10 mg/kg cisplatin demonstrated a loss of weight, indicating drug toxicity at this dosage level. In contrast, mice receiving 10 mg/kg and 15 mg/kg of the PAP-cyc-Pt compound continued to gain weight.

IV. Method of Administration of the Polymer-Platinum Compound

In another aspect, the invention includes a method of targeting a platinum species to a tumor in a subject. The method includes preparing a polymer-platinum compound composed of a diamidodiamine polymer linked to a platinum species. The platinum species is released from the polymer to yield a platinum species which has, or is converted in vivo to have, anti-tumor activity. The polymer-platinum compound is administered to the subject in a therapeutically effective amount.

For administration, the compound can be formulated in a variety of ways. For parenteral administration, the polymer-platinum compound is dissolved in an aqueous medium, e.g., isotonic saline, at a desired platinum concentration. The compound can be administered parenterally as a single bolus dose or as a slow infusion. Alternatively, the compound can be formulated for oral administration by preparation of tablets, elixirs, suspensions and the like.

Appropriate dosages for tumor treatment are determined based on the data presented herein for in vivo administration to tumor-bearing mice. This information, in combination with the known dosages for other platinum species, such as cisplatin and carboplatin, and the relationship in toxicity between these conventional platinum compounds and the polymer-platinum of the present invention, provide guidance for selection of appropriate therapeutic dosages in humans. Adjusting dosages to account for the reduced toxicity of the polymer-platinum compounds is readily done experimentally by one of skill in the art.

Chemotherapy using the polymer-platinum compounds of the present invention in combination with other chemotherapeutic agents may also be suitable for some types of cancers. For example, vinblastine, bleomycin, actinomycin, adriamycin, prednisone or vincristine can be administered with the polymer-platinum compound. As an example, therapy of ovarian cancer may include administration of a therapeutically effective dosage of the polymer-platinum compound and adriamycin coadministered as a 24-hour infusion.

From the foregoing, it can be appreciated how various features and objects of the invention are met. The polymer-platinum compounds of the present invention provide a pharmaceutically acceptable form of platinum for tumor treatment. The polymers are biodegradable which allows for a wide range of molecular weight to be administered intravenously. The polyamidoamine-platinum compounds provide approximately an equivalent therapeutic activity to cisplatin, as evidenced by the i.p. tumor model, but are less toxic. The compounds also provide a means for carrying a high platinum content. The water-solubility and stability of the polymers makes them especially suitable for pharmaceutical preparations.

EXAMPLES

The following examples illustrate preparation of the polymer-platinum compounds of the invention and characterization of the compounds. It will be appreciated that the Examples are illustrative and do not limit the invention in any way.

V. Materials

I. Chemicals

Cisplatin (cis-diamminedicholorplatinum(II)) and o-phenylenediamine were supplied by Sigma UK. All solvents were supplied by Sigma UK and were either distilled or dried over molecular sieves prior to use.

2. Cell Lines

The cell lines used, L132 (human embryonic lung cells), COR L23 (non-small cell lung cancer cells) and H69 (small cell lung cancer), were obtained from European Collection of Cell Cultures, Centre for Applied Biology, Microbiology and Research, Salisbury, Wiltshire UK.

VI. Methods

1. Atomic Absorption Spectroscopy (AAS)

Atomic absorption (flame) was performed using a Perkin-Elmer 280 instrument (Perkin-Elmer, Norwalk, Conn.) calibrated with aqueous solutions of potassium tetrachloroplatinate ($K_2PtCl_4$) or cisplatin ($Pt(NH_3)_2Cl_2$) in concentrated nitric acid, concentrated hydrochloric acid, and hydrogen peroxide (30%).

2. o-Phenylenediamine Colorimetric Assay (o-PDA)

Samples containing 1–5 mg of unknown platinum content were dissolved in 1 ml double distilled water and 1 ml o-phenylenediamine (o-PDA) solution in dimethylformamide (DMF) (1–2 mg/ml) and incubated for 10 minutes at 100° C. The amount of platinum present in the sample was determined by measuring the absorbance at 703 nm using cisplatin as a reference.

Example 1

Synthesis of poly(bisacrylamido-acetoxy-niperazinyl): PACP 2,2-bis acrylamido-acetic acid sodium salt (22.02 g, 0.1 mol) was dissolved in water (100 ml). The solution was carefully purged with nitrogen and cooled to 10° C. by means of an external bath. 2-methylpiperazine (10.02 g, 0.1 mol) was then added. The mixture was then flushed again with nitrogen, and the reaction vessel transferred in a bath maintained at 25° C. After standing at this temperature with occasional hand-stirring for 5 days, the reaction mixture was diluted with water, acidified to pH of approximately 3 with hydrochloric acid, and ultrafiltered through a membrane (Amicon, Danvers, Mass.) with a declared cut-off 3,000. The fraction retained was finally lyophilized. The yield was approximately 23 g. The reaction scheme is illustrated in FIG. 2.

In an alternative procedure to acidification for isolating the polymeric product, the reaction mixture was diluted with acetone (400 ml), and the precipitate was decanted and washed with a fresh portion of acetone (100 ml). In the acidification procedure, aminic nitrogens of the product were in the form of HCl and the carboxyl groups were free, while in the latter procedure using acetone, the aminic groups were free and the carboxyl groups were in the sodium salt form. In either procedure, the product was dried to constant weight at 20° C. and 0.1 Torr.

Example 2

Synthesis of poly(bisacrylamido-acetoxy-aminoCy.dex-piperazinyl): PACP-cyc

A solution of 2,2'-bis-acrylamido-acetic acid sodium (2.202 g, 0.01 mol) in water (10 ml) was prepared and purged with nitrogen as in Example 1. $\mu$-aminomethyl cyclodextrin (0.0025 mol, determined by potentiometric titration from a pool of samples prepared by known methods and impure of sodium chloride) and 2-methyl piperazine (0.752 g, 0.0075 mol) were then added. Subsequently, the reaction mixture was treated and processed as in Example 1. In particular, the reaction mixture was ultrafiltered through a membrane (Amicon) having a molecular weight cut-off of 3,000 Daltons and the fraction retained wa lyophilized and dried to constant weight at 20° C. and 0.1 Torr. The yield was 4.5 g. The reaction scheme is illustrated in FIG. 3.

Example 3

Synthesis of poly[(bisacryloyl piperazine)-β-aminocyclodextrin-piperazinyl]: PAP-cyc The same procedure as in Example 2 was followed, by substituting 1.942 g (0.01 mol) of 1,4-bis acryloyl-piperazine (prepared as described by Ferutti, P. *Macromolecular Syntheses*, 9:25 (1985)) for the same number of moles of 2,2'-bis acrylamido acetic acid. The product was isolated in the same way described in Examples 1 and 2. The yield was 4.1 g. The reaction scheme is illustrated in FIG. 4.

Example 4

Synthesis of Polyamidoamines-Platinum Compounds

Cis-[PtCl$_2$(NH$_3$)$_2$] (161.1 mg) was dissolved in double distilled water (50 ml) at approximately 50° C. and then cooled to room temperature. To this was added, dropwise, a solution of the poly(amidoamine), prepared as described above in Examples 1–3, (100 mg in 10 ml double distilled water). The mixture was stirred for 3 hours. Using an Amicon "CENTRIPREP" concentrator, the resulting solution was concentrated to 20 ml. The concentrate was made up in volume to 30 ml using double distilled water and then concentrated to 10 ml. This procedure of dilution to 30 ml and concentration to 10 ml was repeated a further two times. The product was then lyophilized to yield a white solid (typical yield was 50 mg).

Example 5

Cytotoxicity of Polyamidoamines

Cells were cultured using standard conditions in microtitre plates. After 24 hours of seeding cells (typically L132 or B16 melanoma) at a density of 1×10$^6$ cells/ml, the test polymers and poly-L-lysine (MW 56,500) as a positive reference were added at various concentrations (0–5 mg/ml). Cells were incubated for 72 hours prior to addition of 5-dimethylthiazol-2-yl-2,5-diphenyl tetrazolium bromide (MTT: 10 $\mu$l) to the culture medium. The plates were incubated for a further 5 hours, the medium was removed and 100 $\mu$l of dimethylsulfoxide (DMSO) was added to dissolve the dark blue crystals. Absorbance at 550 nn was measured using a microtitre plate reader and the viability of the test cultures was expressed as a percentage of control incubation in the absence of polymer. The results are shown in FIG. 6 for PACP and in FIGS. 8–9 for the polyamidoamine-Pt compounds.

Example 6

In vitro release of Pt from Polyamidoamine-Platinum Compounds

The polyamidoamine-platinum compounds prepared as described above in Example 4, were dissolved in citrate phosphate buffer or phosphate buffered saline (PBS) at pH 5.5 and pH 7.4, respectively, and dialyzed against the respective solution at 37° C. Samples were taken regularly from the dialysate over 48 hours and free Pt analyzed using the o-PDA assay or by AAS as described above. The concentration of the Pt released from the polymer-platinum compounds was expressed as a percentage of the total available and results are shown in FIGS. 7A–7C.

Example 7

In vitro Cytotoxicity of Polyamidoamine-Platinum Compounds

The MTT assay, described above in Example 5, was used to measure cytotoxicity of free cisplatin and polyamidoamine-platinum compounds toward the lung cell lines; L132, COR L23 and H69. The concentration of polymer-platinum compound required to produce a 50% decrease in cell viability (IC$_{50}$) was calculated, with the results shown in FIGS. 8 and 9 and Table 2.

Example 8

Evaluation of Anti-tumor Activity and Toxicity of Polyamidoamine-Platinum Compounds and Free Cisplatin In Vivo All animal experiments were conducted according to the UKCCCR (United Kingdom Coordinating committee on Cancer Research) Guidelines.
1. L1210 i.p. Tumor Model 10$^6$ viable cells were administered to DBA$_2$ mice (male 9–12 weeks, 20–30 g) i.p. on day 0. Animals were subsequently treated with either single or multiple intraperitoneally-administered doses on days 1, 2 and 3 of cisplatin, of the polyamidoamine polymer PACP alone, or of PAP-cyc-Pt. Animals were weighed daily and observed twice a day for signs of tumor progression and sacrificed if their body weight fell below 80% of the starting weight or if other severe toxicological problems were seen. At the end of the experiment changes in gross anatomy were noted. The results are shown in Table 3 and FIG. 10.

2. B16 Melanoma i.p. Model

Male C57BL/6J mice were inoculated with $10^6$ viable B16F10 cells intraperitoneally (i.p). The cells were injected on day 0 and free cisplatin or PAP-cyc-Pt was injected as i.p. on the following day. Animals were monitored as described above. The results are shown in FIG. 11 and tabulated in Table 4.

Although the invention has been described with respect to particular embodiments, it will be apparent to those skilled in the art that various changes and modifications can be made without departing from the invention.

It is claimed:

1. An anti-tumor composition, comprising
    a complex formed between a platinum species and a biodegradable, water-soluble, diamido-diamine polymer, wherein said complex releases the platinum species from the complex when administered to a patient to yield a platinum species which has, or is converted in vivo to have, anti-tumor activity, and;
    a pharmaceutically-acceptable carrier.

2. The composition of claim 1, wherein said polymer has a structure containing the following monomeric units:

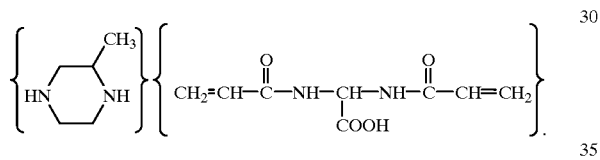

3. The composition of claim 1, wherein said polymer has a structure containing the following monomeric units:

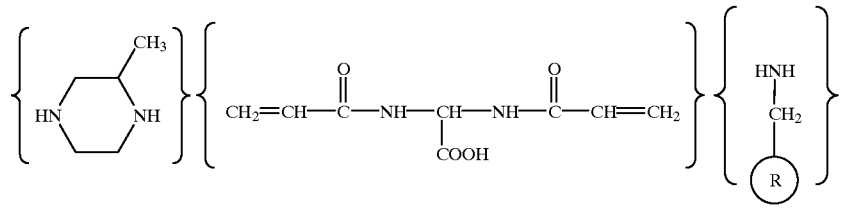

wherein R is an oligosaccharide.

4. The composition of claim 1, wherein said polymer has a structure containing the following monomeric units:

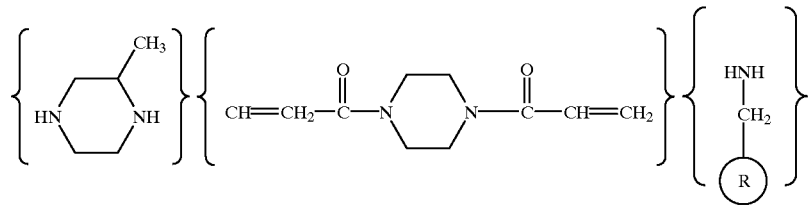

where R is an oligosaccharide.

5. The composition of claim 1, wherein said platinum species is bound to a carboxyl group in the polymer.

6. The composition of claim 1, wherein said platinum species is linked by hydrogen bonds to an oligosaccharide linked to the polymer, wherein the oligosaccharide is derivatized to include a pendant group suitable for hydrogen bonding.

7. The composition of claim 1, wherein said carrier is an aqueous medium suitable for parenteral administration.

8. A method of treating a solid tumor in a subject, comprising
    administering a pharmaceutically effective amount of the anti-tumor composition of claim 1 in a suitable carrier.

9. The method of claim 8, wherein said polymer has a structure containing the following monomeric units:

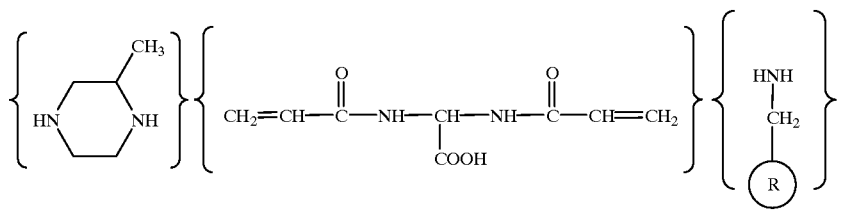

wherein R is an oligosaccharide.

10. The method of claim 8, wherein said polymer has a structure containing the following monomeric units:

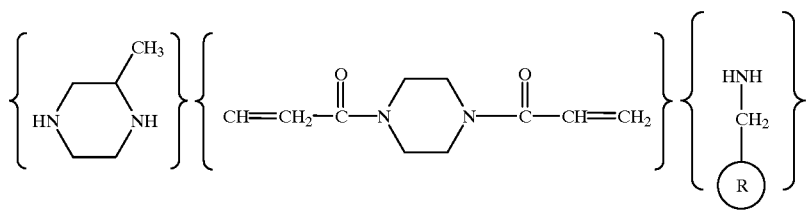

wherein R is an oligosaccharide.

11. The method of claim 8, wherein said polymer has a structure containing the following monomeric units:

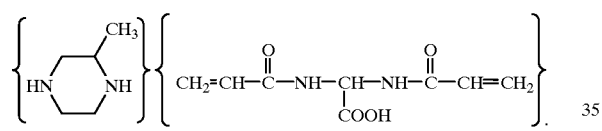

12. The method of claim 8, wherein said platinum species is bound to a carboxyl group in the polymer.

13. The method of claim 8, wherein said platinum species is linked by hydrogen bonds to an oligosaccharide linked to the polymer and derivatized to include functional groups suitable for hydrogen bonding.

14. An anti-tumor compound, consisting of a complex prepared by contacting a platinum species with a biodegradable, water-soluble, diamido-diamine polymer, wherein said complex releases the platinum species from the complex when administered to a patient.

15. The compound of claim 14, wherein said polymer has a structure produced by reacting the following reagents under conditions effective to form a polymer:

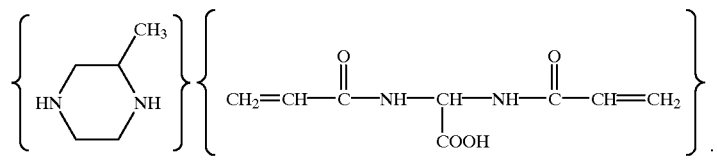

16. The compound of claim 14, wherein said polymer has a structure produced by reacting the following reagents under conditions effective to form a polymer:

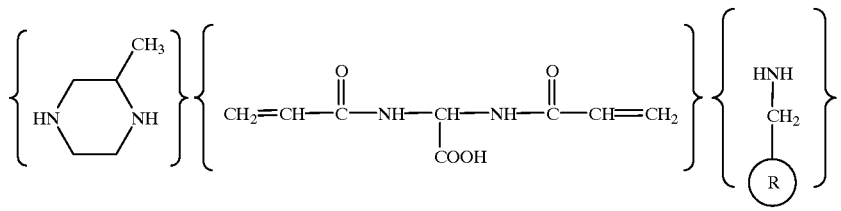

wherein R is an oligosaccharide.

17. The compound of claim 14, wherein said polymer has a structure produced by reacting the following reagents under conditions effective to form a polymer:

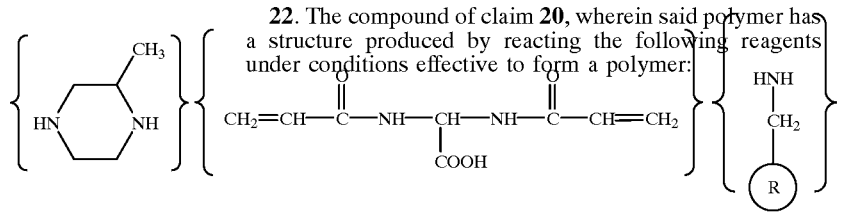

wherein R is an oligosaccharide.

18. The compound of claim 14, wherein said platinum species is bound to a carboxyl group in the polymer.

19. The compound of claim 14, wherein said platinum species is linked by hydrogen bonds to an oligosaccharide linked to the polymer, wherein the oligosaccharide is derivatized to include a pendant group suitable for hydrogen bonding.

20. An anti-tumor compound, consisting of a complex formed between a platinum species and a biodegradable, water-soluble, diamido-diamine polymer, wherein said complex releases the platinum species from the complex when administered to a patient.

21. The compound of claim 20, wherein said polymer has a structure produced by reacting the following reagents under conditions effective to form a polymer:

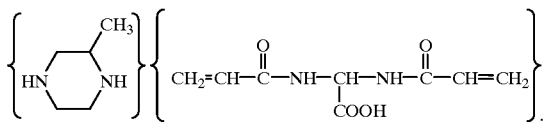

22. The compound of claim 20, wherein said polymer has a structure produced by reacting the following reagents under conditions effective to form a polymer:

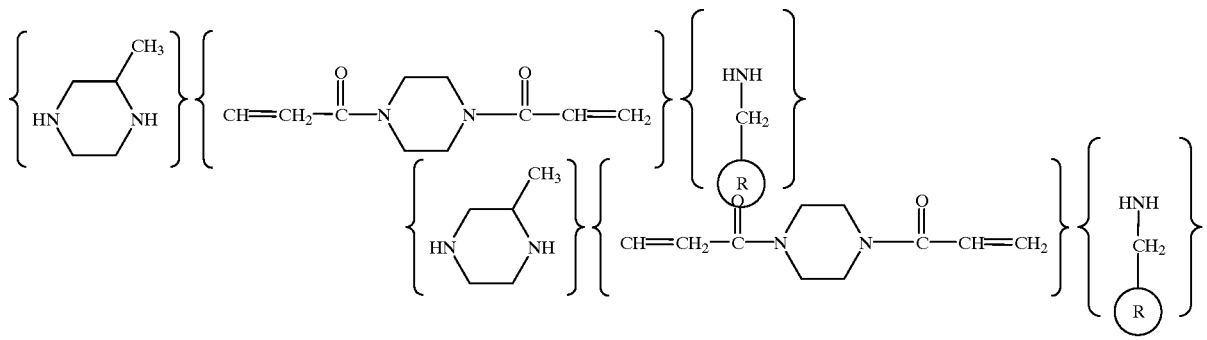

wherein R is an oligosaccharide.

23. The compound of claim 20, wherein said polymer has a structure produced by reacting the following reagents under conditions effective to form a polymer:

wherein R is an oligosaccharide.

24. The compound of claim 20, wherein said platinum species is bound to a carboxyl group in the polymer.

25. The compound of claim 20, wherein said platinum species is linked by hydrogen bonds to an oligosaccharide linked to the polymer and derivatized to include a pendant group suitable for hydrogen bonding.

* * * * *